(12) United States Patent
Tsutsumi

(10) Patent No.: US 6,535,781 B1
(45) Date of Patent: Mar. 18, 2003

(54) APPARATUS FOR MODIFYING COORDINATES

(75) Inventor: Toshiaki Tsutsumi, Yokohama (JP)

(73) Assignee: Semiconductor Leading Edge Technologies, Inc., Yokohama (JP)

( * ) Notice: Subject to any disclaimer, the term of this patent is extended or adjusted under 35 U.S.C. 154(b) by 0 days.

(21) Appl. No.: 09/520,710

(22) Filed: Mar. 8, 2000

(51) Int. Cl.[7] .................. G06F 19/00; G05B 19/18; G01C 17/38; G01P 21/00
(52) U.S. Cl. .................. 700/121; 700/58; 702/95
(58) Field of Search .................. 700/58, 59, 61, 700/64, 194, 121, 110; 702/94, 95, 150, 151; 382/145, 149; 250/310, 398

(56) References Cited

U.S. PATENT DOCUMENTS

| | | | |
|---|---|---|---|
| 4,583,298 A | | 4/1986 | Raugh .................. 33/502 |
| 5,422,724 A | * | 6/1995 | Kinney et al. .................. 356/615 |
| 5,497,007 A | * | 3/1996 | Uritsky et al. .................. 250/491.1 |
| 5,870,187 A | * | 2/1999 | Uritsky et al. .................. 356/237.2 |
| 5,877,035 A | | 3/1999 | Fujino et al. .................. 438/16 |
| 6,124,142 A | * | 9/2000 | Fujino et al. .................. 438/18 |

FOREIGN PATENT DOCUMENTS

JP 8220005 8/1996

* cited by examiner

*Primary Examiner*—Leo Picard
*Assistant Examiner*—Ryan A. Jarrett
(74) *Attorney, Agent, or Firm*—Birch, Stewart, Kolasch & Birch, LLP (57) ABSTRACT

In an apparatus for inspecting and analyzing a particle on a wafer, which causes defect of an integrated circuit, the invention aims to improve the precision of the coordinate of the particle to facilitate the analysis of the particle. As a result, the generation of the particle can be reduced and the yield of the integrated circuit can be increased.

A coordinate modifying apparatus of the invention includes a parameter calculating unit 40 for calculating a coordinate modification parameter, a parameter memory 60 for storing the coordinate modification parameter, and a coordinate modifying unit 70 for correcting the coordinate using the coordinate modification parameter.

7 Claims, 10 Drawing Sheets

APPARATUS FOR MODIFYING COORDINATES

FIELD OF THE INVENTION

The present invention relates to a coordinate modifying apparatus for modifying coordinates between two apparatuses, in particular, to a coordinate modifying apparatus used for apparatuses or systems including such as an apparatus for inspecting and analyzing particle, namely, contamination on the substrate on which subtle pattern is to be formed.

DESCRIPTION OF RELATED ART

Wiring as well as wiring interval of devices has been more subtilized due to the higher integration of the semiconductor integrated circuit (LSI). In case of submicron or sub-quarter-micron applied for wiring, yield is much affected by a minute particle (contamination), which conventionally may not have caused to generate the defect. In a 300 mm wafer process, that is, the enlargement process of the wafer size, which has been recently investigated and developed for reducing the device cost, it is a very important problem how to eliminate the particle generating defect. Therefore, in the LSI process, evaluation and analysis technique of the particle, which causes the defect of the device, using particle analyzers such as an electron microscope, a focused ion beam microscope, microscopic fluorescent spectrochemical analyzer becomes more and more important to search cause of generation of the particle and to eliminate the particle.

A wafer surface inspection apparatus optically detects the particle on the wafer and clarifies the size and the location of the particle, which dominantly promotes the elimination of the particle. The wafer surface inspection apparatus and the particle analysis apparatus (hereinafter, referred to as a wafer surface inspection/analysis apparatus) is indispensable to yielding the integrated circuit.

Figure 11:
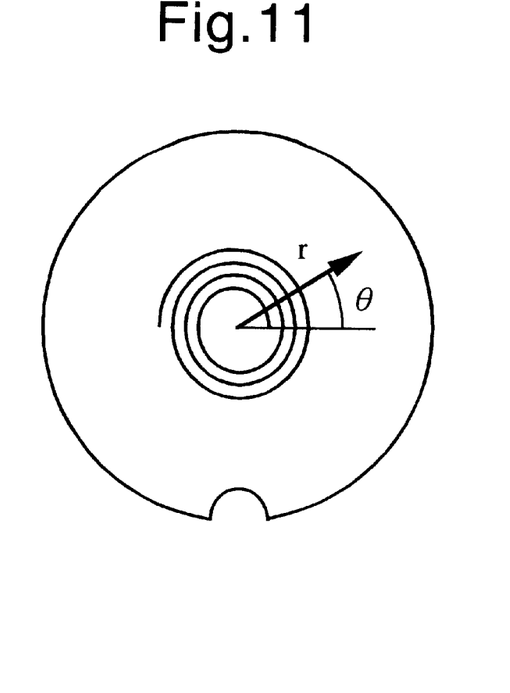
FIG. 11 is a model drawing showing the coordinate system of the wafer surface inspection apparatus.

As shown in FIG. 11, the wafer surface inspection apparatus generally detects contamination on the wafer surface by horizontally moving the wafer with rotating the wafer and spirally scanning the wafer surface by laser beam.

Figure 12:
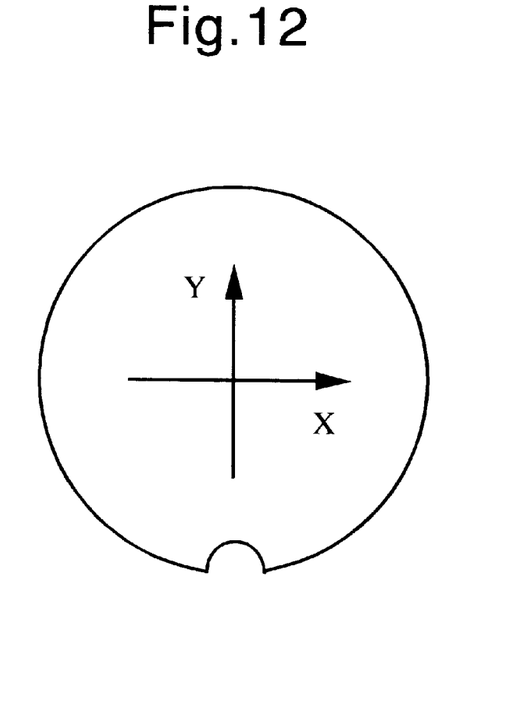
FIG. 12 is a model drawing showing the coordinate system of the particle analysis apparatus.

On the other hand, as shown in FIG. 12, the microscope such as SEM (electron microscope) or FIB (focused ion beam microscope) used for observing the shape and analyzing the component of the particle observes and analyzes the microscopic region by moving the wafer in both horizontal and vertical directions (X-Y directions) to analyze the particle detected by the wafer surface inspection apparatus.

Figure 13:
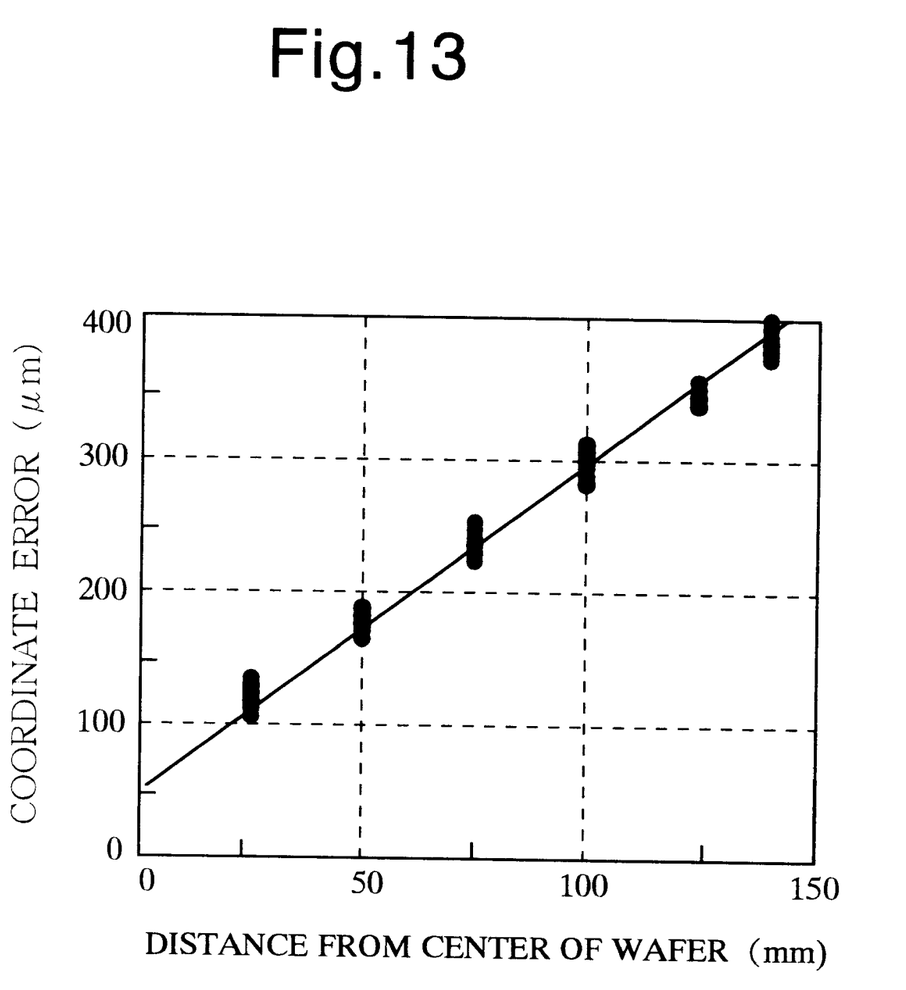
FIG. 13 is a graph showing the relation between the coordinate error and the distance from the center of the wafer.

Between the two apparatuses, different coordinate systems are respectively employed. Accordingly, it is required to have technique or an apparatus for correctly transferring the coordinate data of the particle collected by the wafer surface inspection apparatus to the analysis apparatus such as SEM or FIB device. However, the coordinate error becomes large with directing to the periphery of the wafer as shown in FIG. 13. Namely, the coordinate error becomes large proportionally to the distance from the center of the wafer. This problem becomes more serious according to the enlargement of the wafer size.

A problem to be solved is a problem that the coordinate converting error becomes large proportionally to the distance from the center of the wafer, especially, becomes larger according to the enlargement of the wafer size on transferring the coordinate data from the wafer surface inspection apparatus with the rotary scanning system to the particle analysis apparatus with the scanning system in the X-Y directions.

SUMMARY OF THE INVENTION

The present invention is made to solve the above problem, and aims to provide an apparatus modifying the coordinate using a relation between the coordinate error and the distance from and the angle from the origin of coordinates.

The invention aims, in particular, to improve the precision of the coordinate of the particle on the wafer, which causes the defect of the integrated circuit, and facilitates analyzing the particle in the inspecting/analyzing apparatus of the particle. As a result, the generation of the particle can be reduced and the yield of the integrated circuit can be improved.

DETAILED DESCRIPTION

The present invention provides an inputting function of coordinate modification parameter, a storing function of the parameter, and a modifying function of measured coordinate data based on the coordinate modification parameter as coordinate modification so as to improve the precision of the coordinate.

Further, in order to calculate the coordinate modification parameter, for example, by applying the method of least squares, using the coordinate of marking location of a calibration sample wafer and the coordinate data of the wafer surface inspection apparatus, the invention provides an inputting function of coordinate of a marking location, a storing function of coordinate of the marking location, an inputting function of measured coordinate data of a marking location of a calibration sample wafer measured by the wafer surface inspection apparatus, a storing function of the measured coordinate data, and a calculating function of the coordinate modification parameter based on a relation between the coordinate of the marking location and the measured coordinate data. Therefore, the extraction of the coordinate modification parameter can be facilitated, and the modification of variation of the coordinate modification parameter due to the life time of the apparatus can be also facilitated.

The above coordinate modifying function and the coordinate modification parameter calculating function can be installed in any one of the wafer surface inspection apparatus (an example of the first apparatus), the particle analysis apparatus (an example of the second apparatus), or an apparatus for transmitting the coordinate data conversion from the wafer surface inspection apparatus to the particle analysis apparatus. The functions can be installed in a system including at least two of these apparatuses.

Embodiment 1

Figure 1:
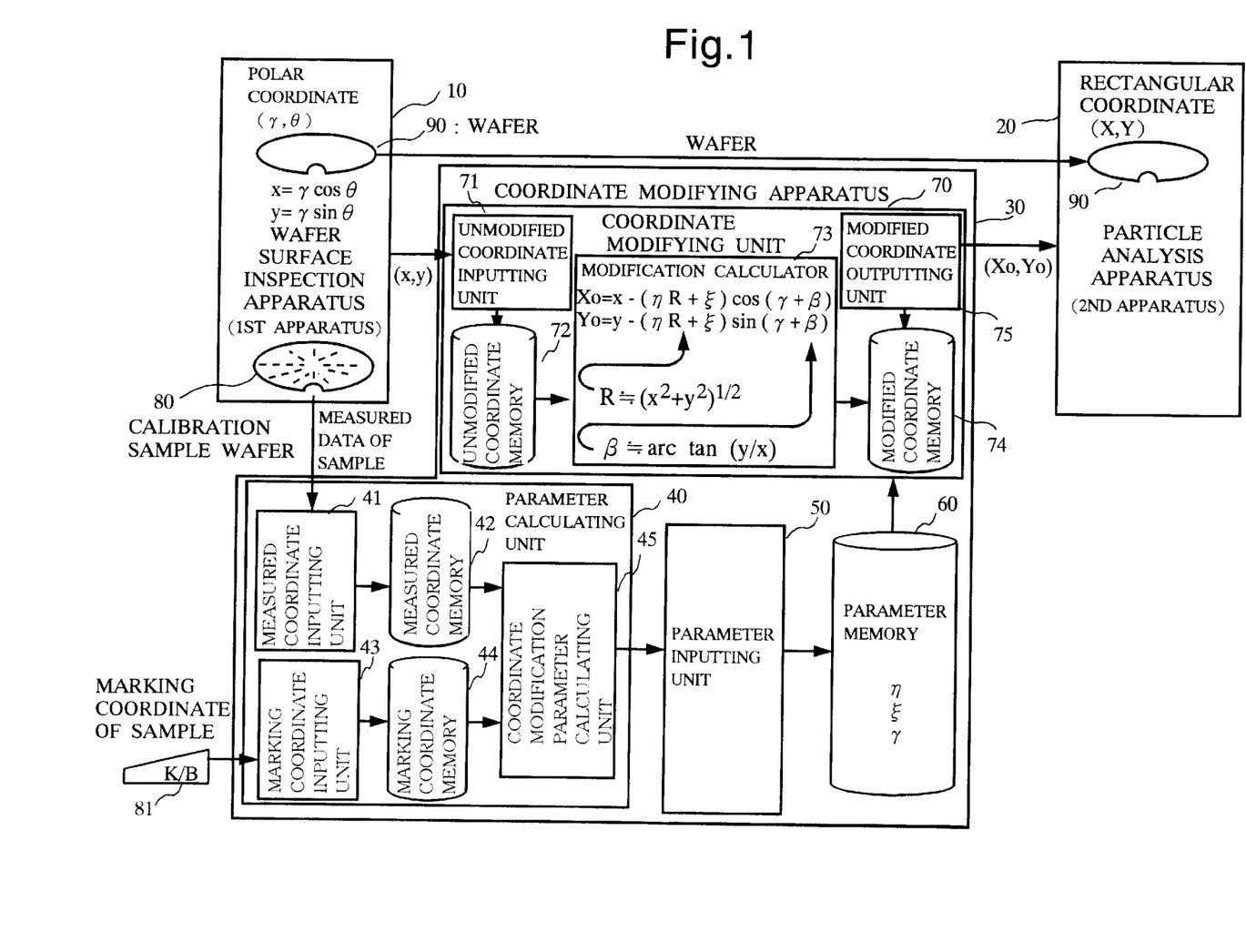
FIG. 1 shows a configuration of a coordinate modifying apparatus according to the present invention.

FIG. 1 shows an example of the coordinate modifying apparatus according to the invention. A reference numeral 10 shows a wafer surface inspection apparatus (an example of the first apparatus) inspecting the surface of the wafer 90 using a polar coordinate system. A reference numeral 20 shows a particle analysis apparatus (an example of the second apparatus) analyzing the particle on the wafer 90 using a rectangular coordinate system. A coordinate modifying apparatus 30 inputs the coordinate (x, y) output from the wafer surface inspection apparatus 10, removes the coordinate error, and outputs the modified coordinate ($X_o$, $Y_o$) to the particle analysis apparatus 20. Inside of the coordinate modifying apparatus 30, there are a parameter calculating unit 40 for calculating parameters for modifying the coordinate, a parameter inputting unit 50 for inputting the parameter, a parameter memory 60 for storing the parameter, and a coordinate modifying unit 70 for modifying the coordinate using the stored parameter. The parameter calculating unit 40 calculates the parameter using the data obtained from a calibration sample wafer 80 (an example of the calibration sample). Marking is made on the calibration sample wafer 80. A measured coordinate inputting unit 41 inputs the coordinate data of the marking on the calibration sample wafer 80 measured by the wafer surface inspection apparatus 10, and stored the input coordinate data in a measured coordinate memory 42.

On the other hand, a marking coordinate inputting unit 43 inputs the marking coordinate of the calibration sample wafer 80 using, for example, an inputting apparatus such as a keyboard 81, and stores the input marking coordinate in a marking coordinate memory 44. A coordinate modification parameter calculating unit 45 compares the measured coordinate with the marking coordinate and calculates the coordinate modification parameter in a way described later. The calculated parameter is input to the parameter inputting unit 50 and stores in the parameter memory 60.

The coordinate modifying unit 70 inputs the unmodified coordinate from the wafer surface inspection apparatus via an unmodified coordinate inputting unit, and stores the input unmodified coordinate in an unmodified coordinate memory 72. A modification calculator 73 modifies the coordinate error included in the unmodified coordinate using an expression described later and stores the modified coordinate in a modified coordinate memory 74. A modified coordinate outputting unit 75 outputs the stored modified coordinate to the particle analysis apparatus 20.

The coordinate modifying apparatus 30 modifies the coordinate error included in the unmodified coordinate output from the wafer surface inspection apparatus using the coordinate modification parameter previously calculated using the calibration sample wafer 80 and stored.

In the following, the coordinate modifying apparatus according to the embodiment will be explained in detail.

First, the dependency of the coordinate error on the distance from the center of the wafer will be considered.

As shown in FIGS. 11 and 12, scanning systems of the wafer are different between the wafer surface inspection apparatus and the particle analysis apparatus. That is, the wafer surface inspection apparatus utilizes the polar coordinate system, while the particle analysis apparatus utilizes the rectangular coordinate system. The linkage of the data between the two apparatuses requires conversion from the polar coordinate (r, θ) to the rectangular coordinate (X, Y).

In the following, the coordinate error will be compared between the above two coordinate systems.

The rectangular coordinate (x, y) can be converted from the polar coordinate (r, θ):

$$x = r \cos \theta, y = r \sin \theta \quad (1)$$

Assuming Δx is an error of x in the rectangular coordinate system;

Δy is an error of y in the rectangular coordinate system;

Δr is an error of r in the polar coordinate system; and

Δθ is an error of θ in the polar coordinate system.

From the above assumption, a relation between the two coordinate system can be expressed by the following:

$$\Delta x = \Delta r \cos \theta - r(\sin\theta)\Delta\theta \quad (2)$$

$$\Delta y = \Delta r \sin \theta - r(\cos\theta)\Delta\theta \quad (3)$$

Therefore, $$\Delta x^2 + \Delta y^2 = r^2 \Delta \theta^2 + \Delta r^2 \quad (4)$$

Figure 2:
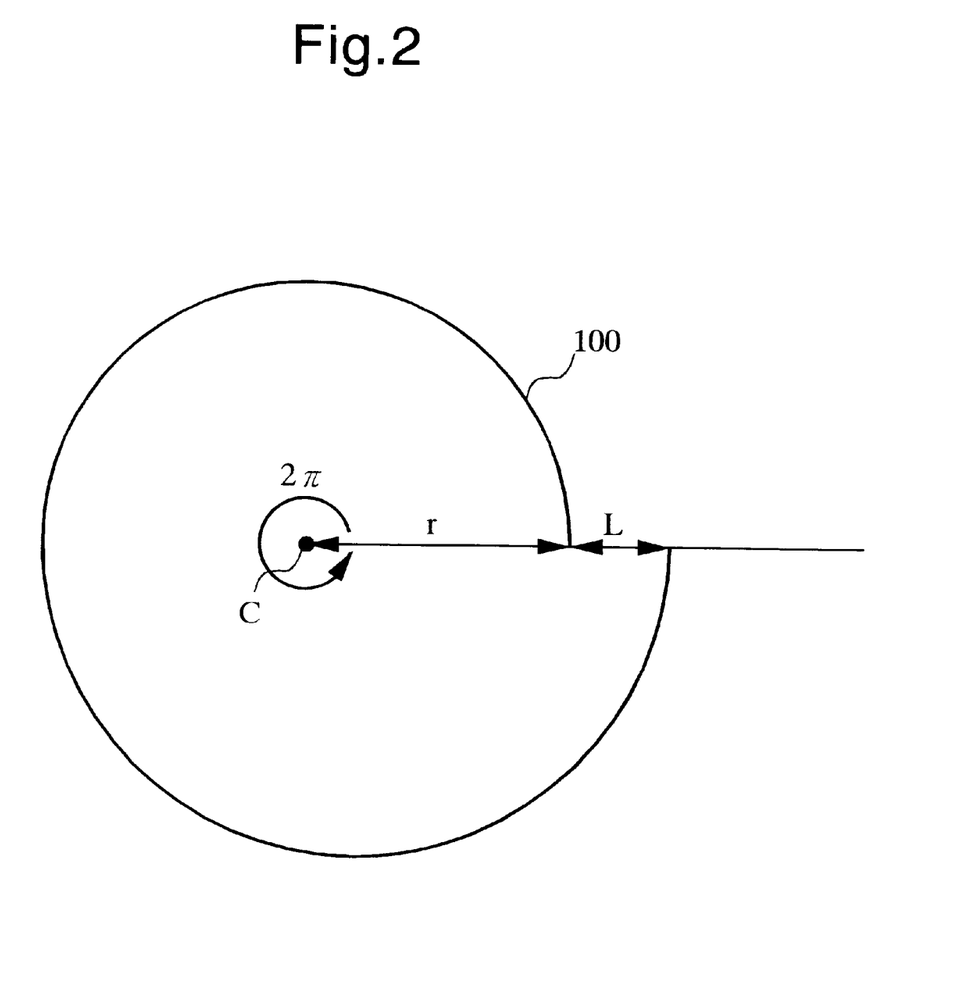
FIG. 2 is a diagram showing spiral scanning of a wafer surface inspection apparatus.

Further, on scanning by laser beam from the center C of the wafer to the periphery, when the radius is r as shown in FIG. 2, an arresting condition is established that one rotation (perimeter=2πr) of a locus 100 will increase the radius r by a predetermined pitch L in the radius direction. Accordingly, the error Δθ is propagated to the error Δr, and the relation becomes Δθ:

2π=Δr: L, namely, Δθ/2π=Δr/L, and the following relation will be established:

$$r\Delta\theta = 2\pi r \Delta r / L \quad (5)$$

Substituted by the expression (5), the expression (4) will be described as 10 follows:

$$\Delta x^2 + \Delta y^2 = ((2\pi r/L)^2 + 1)\Delta r^2 \quad (6)$$

When $(2\pi r/L)^2 \gg 1$, $$\Delta x^2 + \Delta y^2 = (2\pi r/L)^2 \Delta r^2 \quad (7)$$

The expression (7) explains the result of FIG. 13 showing the coordinate error is proportional to the distance from the center. Namely, on converting the polar coordinate into the rectangular coordinate, the coordinate error increases proportionally to the radius r. In FIG. 13, the coordinate error does not pass the origin of the coordinate at the center C (r=0) of the wafer. This is because of an error which has not been considered in the above or mechanical precision and so on.

Figure 3:
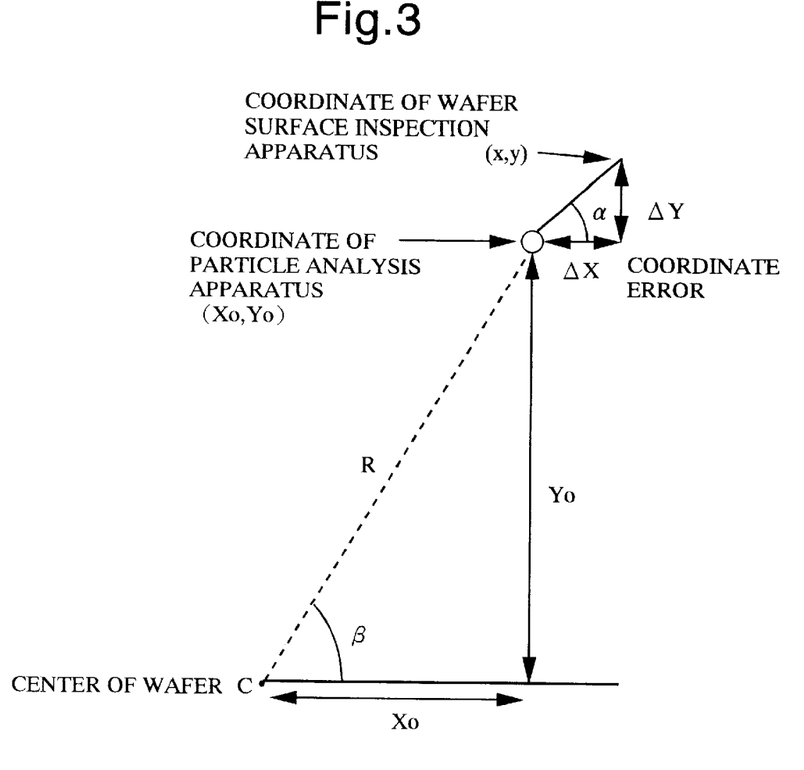
FIG. 3 shows correlation between the coordinate of the wafer surface inspection apparatus and the coordinate of the particle inspection apparatus.

FIG. 3 shows a relation between the coordinate (x, y) of the wafer surface inspection apparatus of the rotary scanning system and the coordinate ($X_o$, $Y_o$) of the particle analysis apparatus of the scanning system in X-Y directions. $\Delta x$ and $\Delta y$ show vectors of the error (hereinafter, referred to as the error vector) between two coordinates of (x, y) and ($X_o$, $Y_o$). $\alpha$ shows an angle parameter showing the direction of the error vector. $\beta$ is an angle parameter showing the location coordinate of the particle analysis apparatus. $\alpha$ is defined by the angle made by the error vector indicated by ($\Delta x$, $\Delta y$) and the x axis, and $\beta$ is defined by the angle made by the vector indicated by ($X_o$, $Y_o$) and the x axis. Among these variables, there are following relations:

$$x = X_o + \Delta x = X_o + (\Delta x^2 + \Delta y^2)^{1/2} \cos \alpha \tag{8}$$

$$y = Y_o + \Delta y = Y_o + (\Delta x^2 + \Delta y^2)^{1/2} \sin \alpha \tag{9}$$

In FIG. 3, R shows the distance from the center of the wafer to ($X_o$, $Y_o$) and $$R = (X_o^2 + Y_o^2)^{1/2} \tag{10}$$

Assuming $\eta$ is the coordinate modification parameter showing a proportional coefficient, and $\xi$ is the coordinate modification parameter showing the error other than r or θ, the following can be said from the expression (7) showing the coordinate error is proportional to the distance R.

$$(\Delta x^2 + \Delta y^2)^{1/2} = \eta R + \xi \tag{11}$$

The expression (11) is a linear equation using the distance R, as a variable, from the center C of the wafer. Namely, the expression (11) shows there is a linear relation between the error vector and the distance from the center of the wafer. In other words, the two coordinate modification parameters $\eta$ and $\xi$ used in the expression (11) are parameters assuming the linear relation between the coordinate error and the origin of the coordinate. In the concrete apparatus, $\Delta x$ and $\Delta y$ are small compared with $X_o$ and $Y_o$, and R is approximately expressed by the following:

$$R = (x^2 + y^2)^{1/2} \tag{12}$$

Next, when the difference between $\alpha$ and $\beta$ is assumed to be $\gamma$, $$\alpha = \gamma + \beta \tag{13}$$

$\alpha$ is an angle showing the direction of the error vector and $\beta$ is an angle showing the direction of the coordinate of the particle analysis apparatus. $\gamma$ is a parameter indicating that the angle $\alpha$ showing the direction of the error vector and the angle $\beta$ showing the direction of the coordinate of the particle analysis apparatus have the linear relation. Further, $\beta$ is given by the following:

$$\beta = \arctan(Y_o/X_o) \tag{14}$$

Here, arc tan is an inverse function of tan.

Since $\Delta x$ and $\Delta y$ are small compared with $X_o$ and $Y_o$, $\beta$ is approximately expressed by the following:

$$\beta = \arctan(y/x) \tag{15}$$

Practically, to correct the coordinate of the particle, since only the coordinate data (x, y) of the wafer surface inspection apparatus is obtained, R and $\beta$ can be given using the expressions (12) and (15), and the coordinate can be corrected as follows:

$$X_o = x - (\eta R + \xi)\cos(\gamma + \beta) \tag{16}$$

$$Y_o = y - (\eta R + \xi)\sin(\gamma + \beta) \tag{17}$$

The coordinate modifying unit 70 shown in FIG. 1 modifies the coordinate using the above expressions (12), (15), (16) and (17).

Here, when the repeatability of the rotation angle of a rotation stage of the wafer surface inspection apparatus is accurate, $\gamma$ becomes a constant.

Accordingly, if the values of the coordinate modification parameters $\eta$, $\xi$ and $\gamma$ are specified, the coordinate error can be modified.

Next, a method for calculating the coordinate modification parameters $\eta$, $\xi$ and $\gamma$ by the parameter calculating unit 40 will be explained in the following.

Figure 5:
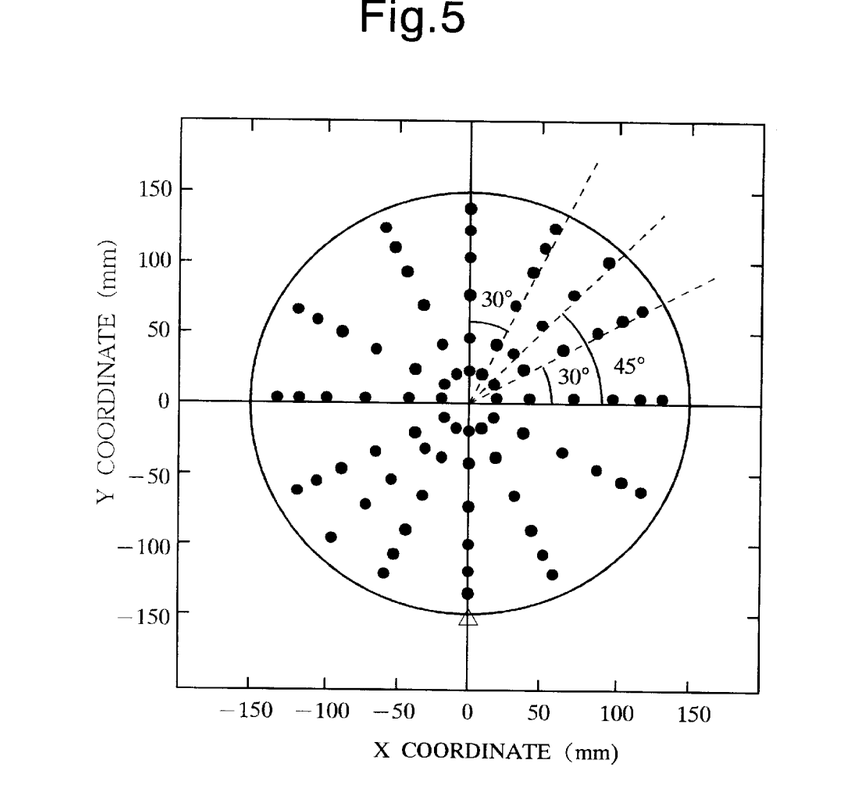
FIG. 5 shows a coordinate of a marking made on a calibration sample wafer of the coordinate.

As shown in FIG. 5, the calibration sample wafer 80 having the marking (a black point in the figure) on the predetermined coordinate is provided. The parameters $\eta$ and $\xi$ can be obtained by comparing the marking coordinate on the calibration sample wafer with the measured coordinate of the wafer surface inspection apparatus and using the dependency of the coordinate error on the distance from the center of the wafer (the origin of the coordinate) and the expression (11). Practically, the parameters can be obtained by the method of least squares. The following shows a concrete example. It is assumed that the coordinate of the i-th marking is (Xoi, Yoi), and the corresponding coordinate measured by the wafer surface inspection apparatus is (xi, yi).

The distance Ri which is from the center to the i-th marking can be obtained by the expression $(Xoi^2 + Yoi^2)^{1/2}$ since the coordinate (Xoi, Yoi) is already known. The difference between the coordinate (xi, yi) and the coordinate (Xoi, Yoi), namely, the error vector ($\Delta xi$, $\Delta yi$) becomes (xi−Xoi, yi−Yoi). Therefore, the parameters $\eta$ and $\xi$ can obtained so as to minimize the value of the following expression:

$$\Sigma\{(\Delta xi^2 + \Delta yi^2)^{1/2} - (\eta Ri + \xi)\}^2 = \Sigma\{((xi-Xoi)^2 + (yi-Yoi)^2)^{1/2} - (\eta(Xoi^2 + Yoi^2)^{1/2} + \xi)\}^2$$

Here, $\Sigma$ indicates a sum of all markings. '$\gamma$ can be obtained similarly using the expression (13) by the method of least squares based on the relation between $\alpha$ and $\beta$.

Figure 4:
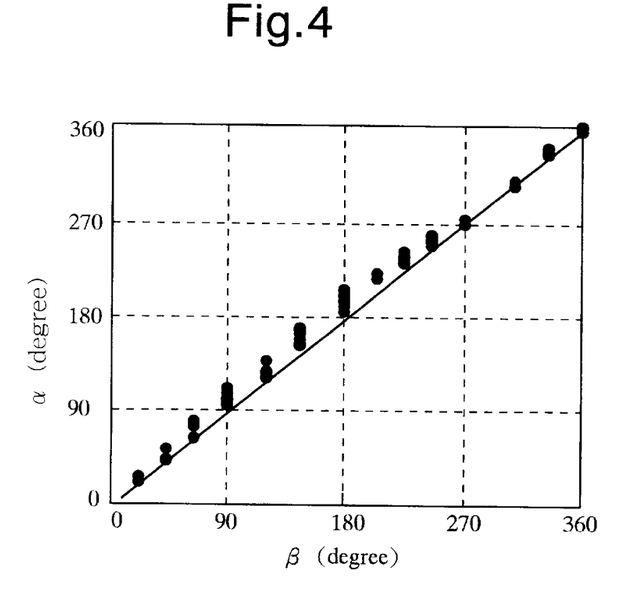
FIG. 4 is a graph showing a relation between the direction of the coordinate of the particle inspection apparatus and the direction of the error vector.

FIG. 4 is a graph showing the relation between $\alpha$ and $\beta$. $\gamma$ can be obtained using FIG. 4 by the method of least squares. The following shows a concrete example.

The angle $\beta i$ of the coordinate of the i-th marking can be obtained by ($\beta i = \arctan(Yoi/Xoi)$ using the expression (14) since (Xoi, Yoi) is already known. The parameter $\gamma$ can be obtained so as to minimize $\Sigma|\alpha i - (\gamma + \beta i)|^2$ since $\alpha i$, which corresponds the i-th marking, is given by $\arctan(\Delta yi/\Delta xi)$. Here, $\Sigma$ indicates a sum of all markings.

As has been described, the coordinate modification parameters can be calculated by the calibration sample wafer having the known coordinate data.

FIG. 5 shows examples of the calibration sample wafer.

In the figure, at the location shown by ●, a marking is made by forming a W film (tungsten film) having thickness of 0.3 $\mu$m by the focused ion beam within the region having a size of 1 $\mu$m×1 $\mu$m. Or, instead of the W film, a cavity having a depth of 1 $\mu$m can be made within the region having a size of 1 $\mu$m×1 $\mu$m. This marking can be formed by a combination of lithography and etching. The values obtained by this example are $\eta = 0.0024$, $\xi = 52.9$ and $\gamma = 2°$.

Figure 6:
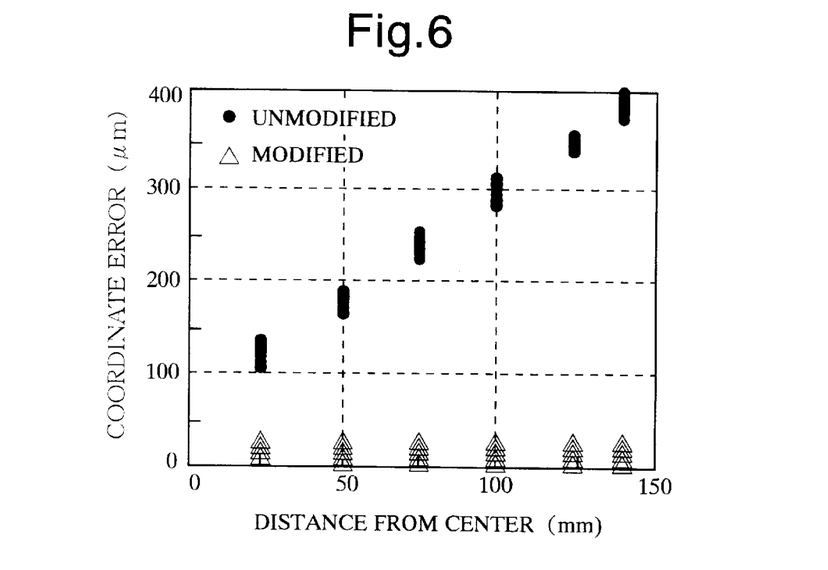
FIG. 6 is a graph showing the dependency of the coordinate on the distance from the center of the wafer of the corrected coordinate using the coordinate correcting method of the present invention.

FIG. 6 shows the dependency of the coordinate error on the distance (R), where ● shows the unmodified coordinate and Δ shows the modified coordinate. Apparently, the coordinate error of the modified coordinate becomes smaller, which shows the precision of the coordinate has been improved.

The expression (11) is obtained from the expression (7) in the above example, in another way, assuming $$(\Delta x^2 + \Delta y^2) = \eta' R^2 + \xi' \qquad (18)$$

and the modification can be operated by the following:

$$Xo = x - (\eta' R^2 + \xi')^{1/2} \cos(\gamma + \beta) \qquad (19)$$

$$Yo = y - (\eta' R^2 + \xi')^{1/2} \sin(\gamma + \beta) \qquad (20)$$

The coordinate modification parameters $\eta'$ and $\xi'$ can be obtained by the method of least squares based on the linear relation of the square of the distance ($R^2$) and the coordinate error.

In the above example, the relation between $\alpha$ and $\beta$ is assumed as the expression (13). However, the relation should be obtained by developing series of trigonometric function of $\beta$ assuming more complex correlation due to the vibration of rotation axis of the wafer and so on. On applying to a concrete device, in most cases, the relation can be sufficiently approximated by one series, namely, a sine function as expressed by the following (21).

$$\alpha = \gamma + \beta + \epsilon \sin \beta \qquad (21)$$

The coordinate modification parameters $\gamma$ and $\epsilon$ can be obtained by the correlation between $\alpha$ and $\beta$. In this case, the expressions for modification are given by the following:

$$Xo = x - (\eta R + \xi) \cos(\gamma + \beta + \epsilon \sin \beta) \qquad (22)$$

$$Yo = y - (\eta R + \xi) \sin(\gamma + \beta + \epsilon \sin \beta) \qquad (23)$$

In another way, $$Xo = x - (\eta' R^2 + \xi')^{1/2} \cos(\gamma + \beta + \epsilon \sin \beta) \qquad (24)$$

$$Yo = y - (\eta' R^2 + \xi')^{1/2} \sin(\gamma + \beta + \epsilon \sin \beta) \qquad (25)$$

In the expressions (13) and (21), the coefficient of $\beta$ is set to 1, however, these expressions can be described more generally using a coefficient other than 1 for multiplying to $\beta$. For example, $\beta$ can be replaced by $\Psi\beta$, and $\Psi$ can be used as another coordinate modification parameter.

Figure 7:
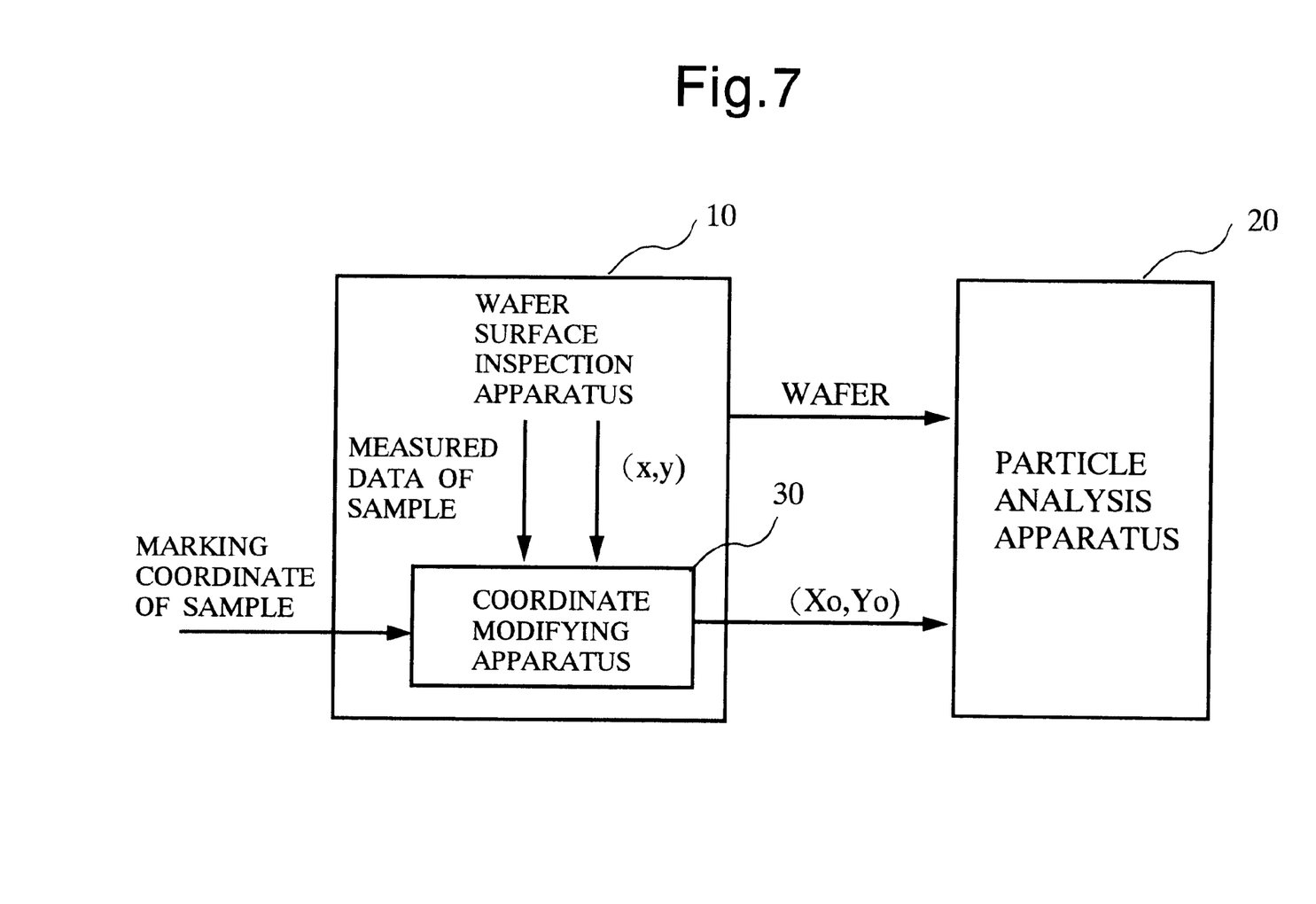
FIG. 7 shows another packaging configuration of the coordinate modifying apparatus 30 of the invention.

FIG. 7 shows a case where the coordinate modifying apparatus 30 is included in the wafer surface inspection apparatus 10.

Figure 8:
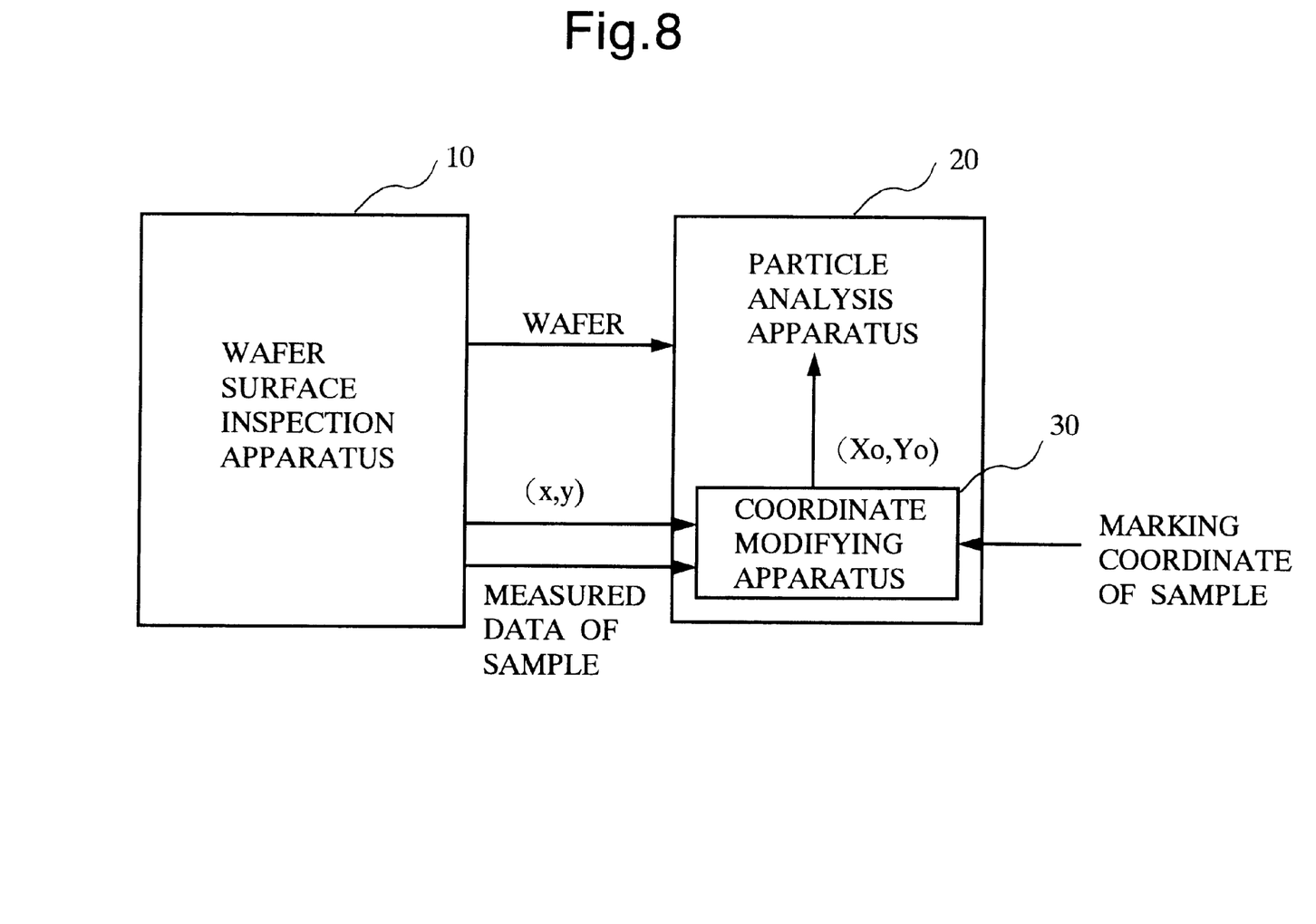
FIG. 8 shows another packaging configuration of the coordinate modifying apparatus 30 of the invention.

FIG. 8 shows a case where the coordinate modifying apparatus 30 is included in the particle analysis apparatus 20.

Figure 9:
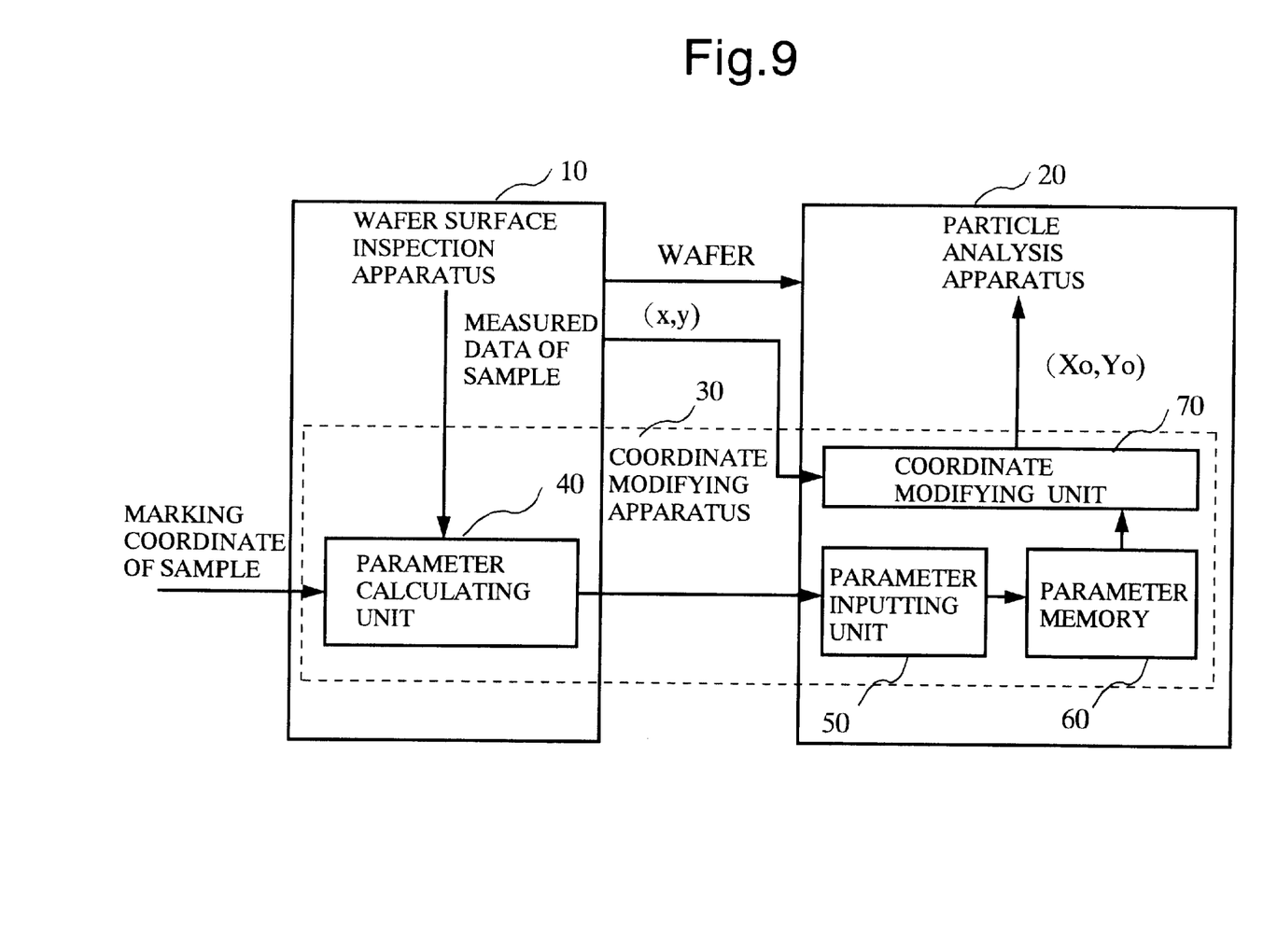
FIG. 9 shows another packaging configuration of the coordinate modifying apparatus 30 of the invention.
Figure 10:
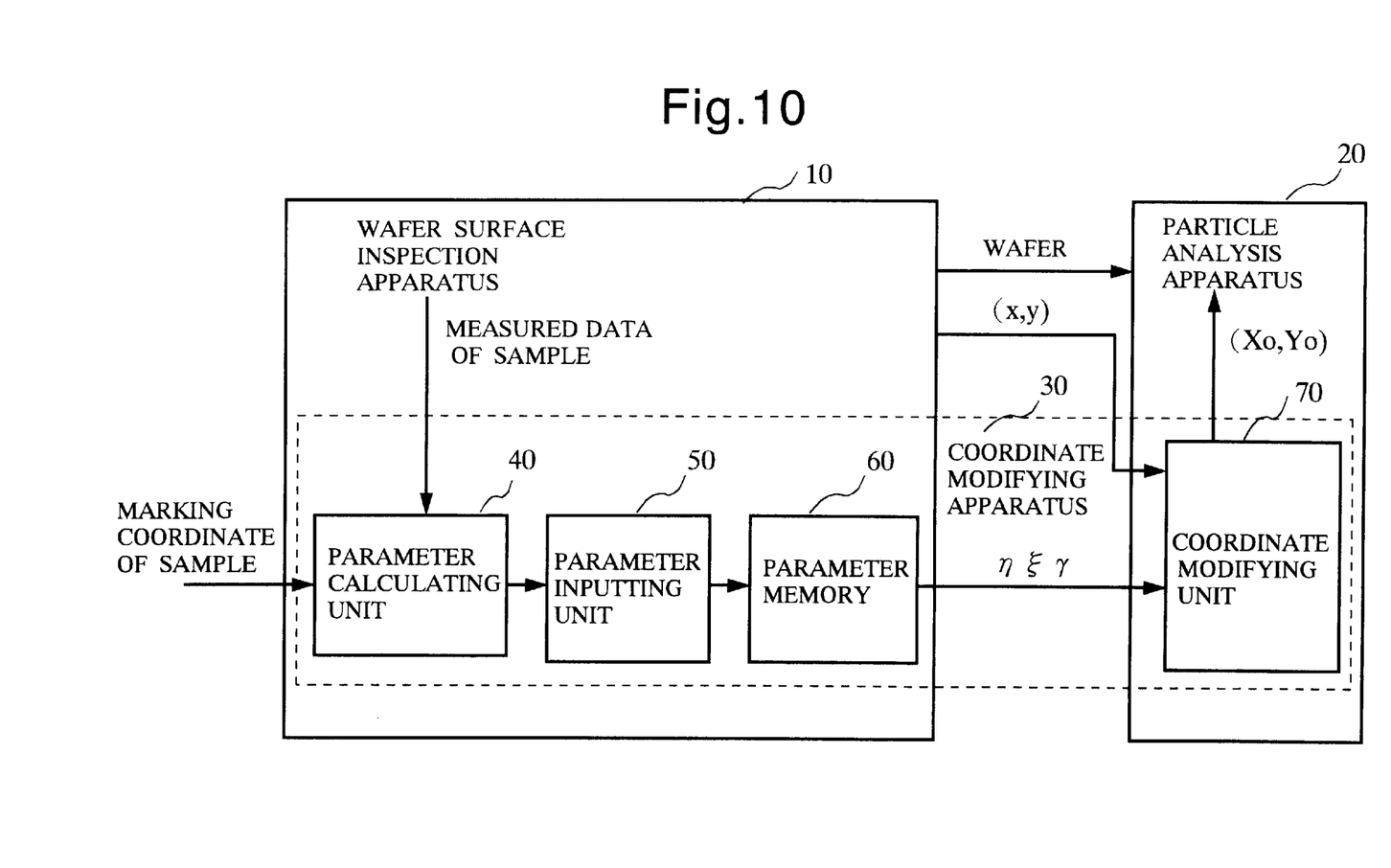
FIG. 10 shows another packaging configuration of the coordinate modifying apparatus 30 of the invention.

FIGS. 9 and 10 show cases where a part of the coordinate modifying apparatus 30 is included in the wafer surface inspection apparatus 10 and 20 the other part of the coordinate modifying apparatus 30 is included in the particle analysis apparatus 20.

The coordinate modifying apparatus 30 can be included in a certain apparatus, and a part of the coordinate modifying apparatus can be included in other apparatus as shown in FIGS. 7 through 10. Further, though it is not shown in the figure, the coordinate modifying apparatus can be included in the transmitter or the receiver.

In the foregoing embodiment, a case where the coordinate modifying apparatus 30 inputs the rectangular coordinate (x, y) has been explained. The coordinate modifying apparatus 30 can be configured so as to input the polar coordinate (r, θ) and to convert into the rectangular coordinate (x, y).

As described above, by applying the present invention to the wafer surface inspection/analysis apparatus, the precision of the coordinate of the particle located on the wafer can be improved and the identification of the particle can be easily performed. By controlling the generation of contamination of the apparatus, the yield of high-quality integrated circuit device can be improved. As a result, the production cost can be reduced.

Further, the increase of the error depending on the distance to the periphery of the coordinate can be controlled by a predetermined simple relational expression between the error resulting from the conversion of the coordinate and the distance from and the angle from the origin of the coordinate.

What is claimed is:

1. A coordinate modifying apparatus inputting a coordinate output from a first apparatus and modifying the coordinate to output as another coordinate for a second apparatus, the coordinate modifying apparatus comprising:
   a parameter memory for storing a coordinate modification parameter for modifying the coordinate; and
   a coordinate modifying unit for modifying the coordinate using the coordinate modification parameter stored in the parameter memory,
   wherein the coordinate modification parameter includes a parameter calculated based on an assumption of a linear relation between a coordinate error and a distance from an origin of the coordinate.

2. The coordinate modifying apparatus of claim 1 further comprising a parameter calculating unit for inputting data obtained by a calibration sample supplied from the first apparatus, calculating the coordinate modification parameter based on the data input, and outputting the coordinate modification parameter to the parameter memory.

3. The coordinate modifying apparatus of claim 2, wherein the parameter calculating unit comprises:
   a marking coordinate inputting unit for inputting a coordinate of a marking made on the calibration sample;
   a marking coordinate memory for storing the coordinate of the marking input;
   a measured coordinate inputting unit for inputting a coordinate of the marking made on the calibration sample measured by the first apparatus;
   a measured coordinate memory for storing the measured coordinate input; and
   a coordinate modification parameter calculating unit for calculating the coordinate modification parameter using the coordinate of the marking stored and the measured coordinate stored.

4. The coordinate modifying apparatus of claim 1, wherein the coordinate modification parameter includes a parameter calculated based on an assumption of a linear relation between a coordinate error and a square of a distance from an origin of the coordinate.

5. The coordinate modifying apparatus of claim 1, wherein the coordinate modification parameter includes a parameter calculated based on an assumption of a linear relation between an angle indicated by a direction of a vector of a coordinate error and an angle indicated by a direction of the coordinate of the second apparatus.

6. The coordinate modifying apparatus of claim 1, wherein the coordinate modification parameter includes a parameter calculated based on a relation among an angle indicated by a direction of a vector of a coordinate error, an angle indicated by a direction of the coordinate of the second apparatus and a trigonometric function of the angle indicated by the direction of the coordinate of the second apparatus.

7. The coordinate modifying apparatus of claim 1, wherein the trigonometric function is a sine function.

* * * * *